(12) United States Patent
Carree

(10) Patent No.: US 9,968,068 B2
(45) Date of Patent: May 15, 2018

(54) WILD ROCKET CULTIVAR 89-001 RZ

(71) Applicant: RIJK ZWAAN ZAADTEELT EN ZAADHANDEL B.V., De Lier (NL)

(72) Inventor: Franciscus Hermanus Carree, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days. days.

(21) Appl. No.: 15/466,972

(22) Filed: Mar. 23, 2017

(65) Prior Publication Data

US 2017/0280669 A1   Oct. 5, 2017

Related U.S. Application Data

(60) Provisional application No. 62/316,711, filed on Apr. 1, 2016.

(51) Int. Cl.
    *A01H 5/12*   (2018.01)

(52) U.S. Cl.
    CPC ................................. *A01H 5/12* (2013.01)

(58) Field of Classification Search
    None
    See application file for complete search history.

(56) References Cited

U.S. PATENT DOCUMENTS 9,474,245 B2 *  10/2016  Kunzemann ............. A01H 5/12

* cited by examiner

*Primary Examiner* — David H Kruse
(74) *Attorney, Agent, or Firm* — Vedder Price P.C.; Thomas J. Kowalski; Deborah L. Lu

(57) ABSTRACT

The present invention relates to a *Diplotaxis tenuifolia* seed designated 89-001 RZ, which exhibits a combination of traits including downy mildew resistance, medium to dark grey green leaves, high leaf thickness and very narrow primary lobes. The present invention also relates to a *Diplotaxis tenuifolia* plant produced by growing the 89-001 RZ seed. The invention further relates to methods for producing the wild rocket cultivar, represented by wild rocket variety 89-001 RZ.

22 Claims, 1 Drawing Sheet

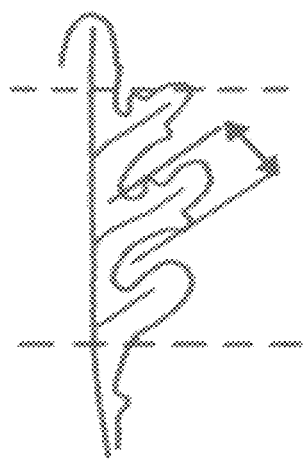

WILD ROCKET CULTIVAR 89-001 RZ

RELATED APPLICATIONS AND INCORPORATION BY REFERENCE

This application claims priority to U.S. provisional patent application Ser. No. 62/316,711, filed Apr. 1, 2016.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated herein by reference, are hereby incorporated herein by reference, and may be employed in the practice of the invention.

FIELD OF THE INVENTION

The present invention relates to a new wild rocket (*Diplotaxis tenuifolia*) variety which may exhibit a combination of traits including downy mildew resistance, medium to dark grey green leaves, high leaf thickness and very narrow primary lobes.

BACKGROUND OF THE INVENTION

Wild rocket (*Diplotaxis tenuifolia*) is a specialty leaf vegetable also known as rucola and arugula. Wild rocket is a quick growing crop grown for its leaves. Due to its pleasant taste it is often used as an ingredient in salads and other dishes.

In many production areas the production of wild rocket is being hindered by the infection of the plants by downy mildew (*Hyaloperonospora parasitica*, previously called *Peronospora parasitica*). Downy mildew is a polycyclic disease caused by different species of the oomycete *Hyaloperonospora*. The obligate parasite from the genus *Hyaloperonospora* is living on Brassica plants and related cruciferous crops. The losses are more severe at the seedling stage than on mature healthy plants. Young seedlings can die as a result of the infection. Cool and moist conditions are favorable for the disease development. The disease causes quantitative and qualitative losses of the crops. Although all (aerial) parts of the plant can be infected, the symptoms primarily appear on the leaves. Symptoms of the disease such as discolored lesions and necrotic spots with brown edges can destroy the quality of the leaves. Also the quantity of the harvest is reduced due to the downy mildew infection.

Citation or identification of any document in this application is not an admission that such document is available as prior art to the present invention.

SUMMARY OF THE INVENTION

There exists a need, therefore, for a wild rocket variety which exhibits a combination of traits including downy mildew resistance, medium to dark grey green leaves, high leaf thickness and very narrow primary lobes.

The present invention addresses this need by providing a new type of wild rocket (*Diplotaxis tenuifolia*) variety, designated 89-001 RZ. Wild rocket cultivar 89-001 RZ exhibits a combination of traits including downy mildew resistance, medium to dark grey green leaves, high leaf thickness and very narrow primary lobes.

The present invention provides a seed of wild rocket variety 89-001 RZ, a sample of seed of said variety having been deposited with the National Collections of Industrial, Marine and Food Bacteria (NCIMB) in Bucksburn, Aberdeen AB21 9YA, Scotland, UK and having been assigned NCIMB Accession No. 42516.

The invention further relates to a plant grown from said seed of wild rocket variety 89-001 RZ.

In one embodiment, the invention relates to a plant grown from said seed of wild rocket variety 89-001 RZ, which is a plant grown from seed having been deposited under NCIMB Accession No. 42516.

In one embodiment, the invention provides a wild rocket plant, or a part thereof, having all the physiological and morphological characteristics of wild rocket variety 89-001 RZ, a sample of seed of said variety having been deposited under NCIMB Accession No. 42516.

In one embodiment, the invention provides a wild rocket plant designated 89-001 RZ, representative seed of which have been deposited under NCIMB Accession No. 42516, wherein said wild rocket plant may comprise a combination of traits including downy mildew resistance, medium to dark grey green leaves, high leaf thickness and very narrow primary lobes.

In one embodiment, the invention provides a wild rocket plant designated 89-001 RZ, representative seed of which have been deposited under NCIMB Accession No. 42516.

In one embodiment, the invention provides for a wild rocket plant which may comprise genetic information for so exhibiting a combination of traits including downy mildew resistance, medium to dark grey green leaves, high leaf thickness and very narrow primary lobes, wherein the genetic information is as contained in a plant, representative seed of which having been deposited under NCIMB Accession No. 42516.

In one embodiment, the invention provides for a wild rocket plant exhibiting a combination of traits downy mildew resistance, medium to dark grey green leaves, high leaf thickness and very narrow primary lobes, and having the genetic information for so exhibiting the combination of traits, wherein the genetic information is as contained in a plant, representative seed of which having been deposited under NCIMB Accession No. 42516.

In an embodiment of the present invention, there also is provided a part of a wild rocket plant of the invention, which may include a part of a wild rocket plant exhibiting a combination of traits including downy mildew resistance, medium to dark grey green leaves, high leaf thickness and very narrow primary lobes, or a part of a wild rocket plant having any of the aforementioned resistance(s) and a combination of traits including one or more morphological or physiological characteristics tabulated herein, including a part of wild rocket variety 89-001 RZ, wherein the plant part is involved in sexual reproduction, which includes, without limitation, a microspore, pollen, an ovary, an ovule, an embryo sacs or an egg cell and/or wherein the plant part is suitable for vegetative reproduction, which includes, without limitation, a cutting, a root, a stem, a cell or a protoplast and/or wherein the plant part is a tissue culture of regenerable cells in which the cells or protoplasts of the tissue culture are derived from a tissue such as, for example and without limitation, a leaf, pollen, an embryo, a cotyledon, a hypocotyl, a meristematic cell, a root, a root tip, an anthers, a flower, a seed or a stem. The plants of the invention from which such a part may come from include those wherein representative seed of which has been deposited under NCIMB Accession No. 42516 or wild rocket variety or cultivar designated 89-001 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In a further embodiment there is a wild rocket plant regenerated from the above-described plant part or regenerated from the above-described tissue culture. Advantageously such a plant may have morphological and/or physiological characteristics of wild rocket variety 89-001 RZ and/or of a plant grown from seed, representative seed of which having been deposited under NCIMB Accession No. 42516—including without limitation such a plant expressing all of the morphological and physiological characteristics of wild rocket variety 89-001 RZ and/or of a plant grown from seed, representative seed of which having been deposited under NCIMB Accession No. 42516. Advantageously, such a plant demonstrates the traits of downy mildew resistance, medium to dark grey green leaves, high leaf thickness and very narrow primary lobes.

Accordingly, in still a further embodiment, there is provided a wild rocket plant having all of the morphological and physiological characteristics of wild rocket variety 89-001 RZ, representative seed of which having been deposited under NCIMB Accession No. 42516. Such a plant may be grown from the seeds, regenerated from the above-described plant parts, or regenerated from the above-described tissue culture. A wild rocket plant having any of the aforementioned resistance(s), and one or more morphological or physiological characteristics recited or tabulated herein, and a wild rocket plant advantageously having all of the aforementioned resistances and the characteristics recited and tabulated herein, are preferred. Parts of such plants—such as those plant parts above-mentioned—are encompassed by the invention.

In an embodiment of the present invention, the invention relates to a method of vegetatively propagating a plant of wild rocket variety 89-001 RZ which may comprise (a) collecting tissue capable of being propagated from a plant of wild rocket 89-001 RZ, a sample of seed of said variety having been deposited under NCIMB Accession No. 42516, and (b) producing a rooted plant from said tissue.

In one embodiment, there is provided a method for producing a progeny of wild rocket cultivar 89-001 RZ which may comprise crossing the plant designated 89-001 RZ with itself or with another wild rocket plant, harvesting the resultant seed, and growing said seed.

In a further embodiment there is provided a progeny plant produced by sexual or vegetative reproduction, grown from seeds, regenerated from the above-described plant parts, or regenerated from the above-described tissue culture of the wild rocket cultivar or a progeny plant thereof, representative seed of which having been deposited under NCIMB Accession No. 42516. The progeny may have any of the aforementioned resistance(s), and one or more morphological or physiological characteristics recited or tabulated herein, and a progeny plant advantageously having all of the aforementioned resistances and the characteristics recited and tabulated herein, are preferred. Advantageously, the progeny demonstrate the traits of downy mildew resistance, medium to dark grey green leaves, high leaf thickness and very narrow primary lobes.

Progeny of the wild rocket variety 89-001 RZ may be modified in one or more other characteristics, in which the modification is a result of, for example and without limitation, mutagenesis or transformation with a transgene.

In still another embodiment, the present invention provides progeny of wild rocket cultivar 89-001 RZ produced by sexual or vegetative reproduction, grown from seeds, regenerated from the above-described plant parts, or regenerated from the above-described tissue culture of the wild rocket cultivar or a progeny plant thereof, in which the regenerated plant shows a combination of traits including downy mildew resistance, medium to dark grey green leaves, high leaf thickness and very narrow primary lobes.

In still a further embodiment, the invention provides a method of producing a hybrid wild rocket seed which may comprise crossing a first parent wild rocket plant with a second parent wild rocket plant and harvesting the resultant hybrid wild rocket seed, in which the first parent wild rocket plant or the second parent wild rocket plant may be a wild rocket plant of the invention, e.g. a wild rocket plant having a combination of traits including downy mildew resistance, medium to dark grey green leaves, high leaf thickness and very narrow primary lobes and one or more morphological or physiological characteristics tabulated herein, including a wild rocket plant of wild rocket cultivar 89-001 RZ, representative seed of which having been deposited under 42516.

In another embodiment, the invention provides producing a wild rocket plant which may exhibit a combination of traits including downy mildew resistance, medium to dark grey green leaves, high leaf thickness and very narrow primary lobes which may comprise: crossing a mother wild rocket plant with a father wild rocket plant to produce a hybrid seed; growing said hybrid seed to produce a hybrid plant; selfing said hybrid plant to produce F2 progeny seed; growing said F2 progeny seed to produce F2-plants; selecting said F2-plants for exhibiting a combination of traits including downy mildew resistance, medium to dark grey green leaves, high leaf thickness and very narrow primary lobes.

Advantageously the selfing and selection may be repeated; for example at least once, or at least twice, thrice, four times, five times, six times or more, to produce F3 or F4 or F5 or F6 or subsequent progeny, especially as progeny from F2 may exhibit the aforementioned combination of traits, and may be desirable.

In still a further embodiment, the invention provides a method of producing a wild rocket cultivar which may exhibit a combination of traits including downy mildew resistance, medium to dark grey green leaves, high leaf thickness and very narrow primary lobes.

The invention even further relates to a method of producing wild rocket which may comprise: (a) cultivating to the vegetative plant stage a plant of wild rocket variety 89-001 RZ, representative seed of which having been deposited under NCIMB Accession No. 42516, and (b) harvesting wild rocket leaves or heads from the plant. The invention further comprehends packaging and/or processing the wild rocket plants, heads or leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on Jan. 22, 2016, under deposit accession number 42516 was made pursuant to the terms of the Budapest Treaty. Upon issuance of a patent, all restrictions upon the deposit will be removed, and the deposit is intended to meet the requirements of 37 CFR § 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawing, in which:

FIG. 1 is an illustration of how to measure the width of the primary lobes. The width of the primary lobes should be observed in the middle part of the leaf.

DETAILED DESCRIPTION OF THE INVENTION

The invention provides methods and compositions relating to plants, seeds and derivatives of a new wild rocket variety herein referred to as wild rocket variety 89-001 RZ. Wild rocket variety 89-001 RZ is a uniform and stable line, distinct from other such lines.

In a preferred embodiment, the specific type of breeding method employed for developing a wild rocket cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation. Using this pedigree method, two parents may be crossed using an emasculated female and a pollen donor (male) to produce $F_1$ offspring.

Parental varieties are selected from commercial varieties that individually exhibit one or more desired phenotypes. Additionally, any breeding method involving selection of plants for the desired phenotype may be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

A detailed description of the development of wild rocket variety 89-001 RZ is described in Table 1. The seedlot in year 3 was deposited with the NCIMB under deposit number 42516.

TABLE 1

| Year | | Description |
| --- | --- | --- |
| 0 | F1 | Pedigree selection from S 09.67058 |
| 1 | S1F1 | Plant selected and self fertilized |
| 2 | S2F1 | Plant selected and self fertilized |
| 3 | M1S2F1 | Generation grown (in mass) |

In one embodiment, a plant of the invention has all the morphological and physiological characteristics of wild rocket variety 89-001 RZ. These characteristics of a wild rocket plant of the invention, e.g. variety 89-001 RZ, are summarized and compared to its closest publicly available variety in Table 2.

The information presented in Table 2 was determined in trial experiments in accordance with the UPOV TG/244/1 Form (Guidelines for the Conduct of Tests for Distinctness, Uniformity and Stability, International Union for the Protection of New Varieties of Plants). The terminology used in these tables is the official terminology found and defined in the UPOV TG/244/1 as of the filing date, and is thus clear for a person skilled in the art.

TABLE 2

Physiological and morphological characteristics of 89-001 RZ in comparison with closest known variety "Voyager".

| Character | 89-001 RZ | Voyager |
| --- | --- | --- |
| Ploidy | Diploid | Diploid |
| Leaf | | |
| 1. Attitude | Semi-erect (3) | Semi-erect (3) |
| 2. Color of blade | Grey-green (2) | Green (1) |
| 3. Intensity of color | Medium to dark (6) | Light to medium (4) |
| 4. Length | Medium (5) | Medium (5) |

TABLE 2-continued

Physiological and morphological characteristics of 89-001 RZ in comparison with closest known variety "Voyager".

| Character | 89-001 RZ | Voyager |
|---|---|---|
| Ploidy | Diploid | Diploid |
| 5. Width | Narrow to medium (4) | Broad (7) |
| 6. Division | Weak to medium (4) | Medium (5) |
| 7. Width of primary lobes | Very narrow (2) | Narrow to medium (4) |
| 8. Secondary lobing | Medium (2) | Strong (3) |
| 9. Time of flowering Plant | Early to medium (4) | Medium (5) |
| 10. Height at flowering stage | Medium (5) | Long (7) |

Aside from the morphological and physiological characteristics mentioned in Table 2, a plant of the invention also exhibits downy mildew resistance, medium to dark grey green leaves, high leaf thickness and very narrow primary lobes.

As used herein, resistance to downy mildew is defined as the ability of a plant to resist infection by *Hyaloperonospora parasitica*. Under normal disease pressure in the field plants of wild rocket variety 89-001 RZ show no symptoms of downy mildew infection, while under high disease pressure said plants may show some disease symptoms such as the formation of discolored lesions and/or necrotic spots. Resistance is tested by inoculating a relevant number of plants, such as 30, with spores of *Hyaloperonospora parasitica* after having grown the plants for about 2 weeks at a temperature regime of 14/12° C. day/night, and observing symptoms of downy mildew infection, including the formation of discoloured lesions, necrotic spots with brown edges and sporulation, 10 and 17 days later. Plants of wild rocket variety 89-001 RZ occasionally show some disease symptoms such as the formation of discolored lesions and/or sporulation in such a disease test. Wild rocket variety 89-001 RZ exhibits a resistance to *Hyaloperonospora parasitica*.

As used herein, the color and color intensity of the leaf is in concordance with that used on the UPOV TG/244/1 Form. Wild rocket variety 89-001 RZ has medium to dark grey green leaves. On the TG/244/1 Form the color of the leaf blade is determined by visual comparison to standard varieties. Two different leaf blade colors are recognized: grey and grey green. The color of the leaf blade is determined by comparison to standard varieties Nature and Tiger. Nature has a green leaf blade, while Tiger has a grey green leaf blade. The color of the leaf blades of wild rocket variety 89-001 RZ is grey green, as they are most similar in color to those of variety Tiger. On the TG/244/1 Form three different color intensities of the leaf are recognized: light, medium and dark. The color intensity of the leaves of wild rocket variety 89-001 RZ is medium to dark.

As used herein the leaf thickness is by visual comparison to publicly available varieties. High leaf thickness is defined as the leaf thickness being higher than the leaf thickness of publicly available variety Voyager, and slightly lower than the leaf thickness of publicly available variety Olivetta. Wild rocket variety 89-001 RZ has a high leaf thickness which is higher than that of publicly available variety Voyager and slightly lower than that of publicly available variety Olivetta.

As used herein, the width of the primary lobes is in concordance with that used on the UPOV TG/244/1 Form, see also FIG. 1. On the TG/244/1 Form the width of the primary lobes of the leaf is scored in the categories narrow, medium and broad. In comparison with publicly available wild rocket varieties the width of the primary lobes of wild rocket variety 89-001 RZ is exceptionally narrow, therefore wild rocket variety 89-001 RZ is regarded to have very narrow primary lobes.

In an embodiment, the invention relates to a wild rocket plant that has all the morphological and physiological characteristics of the invention and has acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced by backcrossing, useful traits may be introduced directly into the plant of the invention, being a plant of wild rocket variety 89-001 RZ, by genetic transformation techniques; and, such plants of wild rocket variety 89-001 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of wild rocket variety 89-001 RZ or may, alternatively, be used for the preparation of transgenes which may be introduced by backcrossing. Methods for the transformation of plants, including wild rocket, are well known to those of skill in the art.

Vectors used for the transformation of wild rocket cells are not limited so long as the vector may express an inserted DNA in the cells. For example, vectors which may comprise promoters for constitutive gene expression in wild rocket cells (e.g., cauliflower mosaic virus 35S promoter) and promoters inducible by exogenous stimuli may be used. Examples of suitable vectors include pBI binary vector. The "wild rocket cell" into which the vector is to be introduced includes various forms of wild rocket cells, such as cultured cell suspensions, protoplasts, leaf sections, and callus. A vector may be introduced into wild rocket cells by known methods, such as the polyethylene glycol method, polycation method, electroporation, Agrobacterium-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target wild rocket cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of wild rocket variety 89-001 RZ.

Agrobacterium-mediated transfer is another widely applicable system for introducing gene loci into plant cells. An advantage of the technique is that DNA may be introduced into whole plant tissues, thereby bypassing the need for regeneration of an intact plant from a protoplast. Agrobacterium transformation vectors are capable of replication in E. coli as well as Agrobacterium, allowing for convenient manipulations. Moreover, advances in vectors for Agrobacterium-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, Agrobacterium containing both armed and disarmed Ti genes may be used for transformation. In those plant strains where Agrobacterium-mediated transformation is efficient, it is the method of choice because of the facile and defined nature of the gene locus transfer. The use of Agrobacterium-mediated plant integrating vectors to introduce DNA into plant cells, including lettuce plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for wild rocket plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins (psaD, psaF, psaE, PC, FNR, atpC, atpD, cab, rbcS) (see U.S. Pat. No. 7,161,061), the CAB-1 promoter (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the wild rocket variety of this invention include, for example, DNA sequences or genes from another species, or even genes or sequences which originate with or are present in wild rocket species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of wild rocket variety 89-001 RZ. Non-limiting examples of particular genes and corresponding phenotypes one may choose to introduce into a wild rocket plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734, 341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed wild rocket and/or methods of transforming wild rocket or wild rocket plant cells, and techniques from these US Patents, as well as promoters, vectors, etc., may be employed in the practice of this invention to introduce exogenous nucleic acid sequence (s) into a plant of wild rocket variety 89-001 RZ (or cells thereof), and exemplify some exogenous nucleic acid sequence(s) which may be introduced into a plant of wild rocket variety 89-001 RZ (or cells thereof) of the invention, as well as techniques, promoters, vectors etc., to thereby obtain further plants of wild rocket variety 89-001 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. (See generally U.S. Pat. No. 7,041,876).

The invention provides a method of producing a wild rocket seed which may comprise crossing a male parent wild rocket plant with a wild rocket parent plant and harvesting the resultant wild rocket seed, wherein said male parent wild rocket plant and/or said female parent wild rocket plant is the wild rocket plant of grown from a seed of wild rocket variety 89-001 RZ, a sample of seed of said variety having been deposited under NCIMB Accession No. 42516. The invention includes a wild rocket seed produced by this method and a wild rocket plant produced by growing said seed.

Also, the invention comprehends methods for producing a seed of a "89-001 RZ"-derived wild rocket plant which may comprise (a) crossing a plant of wild rocket variety 89-001 RZ, representative seed of which having been deposited under NCIMB Accession No. 42516, with a second wild rocket plant, and (b) whereby seed of a 89-001 RZ-derived wild rocket plant forms. Such a method may further comprise (c) crossing a plant grown from 89-001 RZ-derived wild rocket seed with itself or with a second wild rocket plant to yield additional 89-001 RZ-derived wild rocket seed, (d) growing the additional 89-001 RZ-derived wild rocket seed of step (c) to yield additional 89-001 RZ-derived wild rocket plants, and (e) repeating the crossing and growing of steps (c) and (d) for an additional 3-10 generations to generate further 89-001 RZ-derived wild rocket plants, and (f) whereby seed of a 89-001 RZ-derived wild rocket plant forms.

The invention further relates to the above-described methods that may further comprise selecting at steps b), d), and e), a 89-001 RZ-derived wild rocket plant, exhibiting a combination of traits including downy mildew resistance, medium to dark grey green leaves, high leaf thickness and very narrow primary lobes.

The invention even further relates to a seed produced by the above-described methods.

In particular, the invention relates to methods for producing a seed of a 89-001 RZ-derived wild rocket plant which may comprise (a) crossing a plant of wild rocket variety 89-001 RZ, representative seed of which having been deposited under NCIMB Accession No. 42516, with a second wild rocket plant and (b) whereby seed of a 89-001 RZ-derived wild rocket plant forms, wherein such a method may further comprise (c) crossing a plant grown from 89-001 RZ-derived wild rocket seed with itself or with a second wild rocket plant to yield additional 89-001 RZ-derived wild rocket seed, (d) growing the additional 89-001 RZ-derived wild rocket seed of step (c) to yield additional 89-001 RZ-derived wild rocket plants and selecting plants exhibiting a combination of the traits including downy mildew resistance, medium to dark grey green leaves, high leaf thickness and very narrow primary lobes, and (e) repeating the crossing and growing of steps (c) and (d) for an additional 3-10 generations to further generate 89-001 RZ-derived wild rocket plants that exhibit a combination of traits including downy mildew resistance, medium to dark grey green leaves, high leaf thickness and very narrow primary lobes.

The invention additionally provides a method of introducing at least one new trait into a plant of wild rocket variety 89-001 RZ which may comprise: (a) crossing a plant of wild rocket variety 89-001 RZ, representative seed of which having been deposited under NCIMB Accession No. 42516, with a second wild rocket plant that may comprise at least one new trait to produce progeny seed; (b) harvesting and planting the progeny seed to produce at least one progeny plant of a subsequent generation, wherein the progeny plant may comprise the at least one new trait; (c) crossing the progeny plant with a plant of wild rocket variety 89-001 RZ to produce backcross progeny seed; (d) harvesting and planting the backcross progeny seed to produce a backcross progeny plant; and (e) repeating steps (c) and (d) for at least three additional generations to produce a wild rocket plant of variety 89-001 RZ which may comprise at least one new trait and all of the physiological and morphological characteristics of a plant of wild rocket variety 89-001 RZ, when grown in the same environmental conditions. This method may comprise introducing a mutation or transgene conferring the at least one new trait into a plant of wild rocket variety 89-001 RZ. The invention, of course, includes a wild rocket plant produced by this method.

Backcrossing may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of wild rocket variety 89-001 RZ, representative seed of which having been deposited under NCIMB Accession No. 42516, is used in backcrossing, offspring retaining the combination of traits including downy mildew resistance, medium to dark grey green leaves, high leaf thickness and very narrow primary lobes are progeny within the ambit of the invention. Backcrossing methods may be used with the present invention to improve or introduce a characteristic into a plant of the invention, being a plant of wild rocket variety 89-001 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of wild rocket variety 89-001 RZ, representative seed of which has been deposited under NCIMB Accession No. 42516, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples. This method may additionally comprise the step of storing the results of detecting the plurality of polymorphisms on a computer readable medium. The plurality of polymorphisms are indicative of and/or give rise to the expression of any one or more, or all, of the morphological and physiological characteristics of wild rocket variety 89-001 RZ.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for wild rocket variety 89-001 RZ. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DArT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 Dec. 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PLoS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the characteristic of downy mildew resistance by comparing the genotype and/or the sequence of wild rocket variety 89-001 RZ with the genotype and/or the sequence of one or more reference plants. The reference plant(s) used for comparison in this example may for example be, but is not limited to, the comparison variety Voyager.

The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

The invention relates to a method of producing wild rocket leaves as a food product which may comprise sowing the seed of wild rocket variety 89-001 RZ, and growing the seed into a harvestable wild rocket plant and harvesting the leaves of said plant.

The invention further includes a method for producing wild rocket leaves as a fresh vegetable which may comprise packaging leaves of a plant of wild rocket variety 89-001 RZ, and a method for producing wild rocket leaves as a processed food which may comprise processing leaves of a plant of wild rocket variety 89-001 RZ.

Wild rocket leaves are sold in packaged form, including without limitation as pre-packaged wild rocket salad or as wild rocket heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the wild rocket leaves of the invention. Thus, the invention comprehends the use of and methods for making and using the leaves of the wild rocket plant of the invention, as well as leaves of wild rocket plants derived from the invention. The invention further relates to a container which may comprise one or more plants of the invention, or one or more wild rocket plants derived from a plant of the invention, for harvest of leaves from the plant. This way the consumer may pick very fresh leaves for use in salads. More generally, the invention includes one or more plants of the invention or one or more plants derived from wild rocket of the invention, wherein the plant is in a ready-to-harvest condition, including with the consumer picking his own, and further including a container which may comprise one or more of these plants.

The invention is further described by the following numbered paragraphs:

1. A seed of wild rocket variety 89-001 RZ, a sample of seed of said variety having been deposited under NCIMB Accession No. 42516.

2. A plant grown from the seed of paragraph 1.

3. The wild rocket plant of paragraph 2, which is a plant grown from seed having been deposited under NCIMB Accession No. 42516.

4. A wild rocket plant, or a part thereof, having all the physiological and morphological characteristics of the wild rocket plant of paragraph 2.

5. A part of the plant of paragraph 4, wherein said part is a microspore, pollen, an ovary, an ovule, an embryo sac or an egg cell, a cutting, a root, a stem, a cell or a protoplast.

6. A tissue culture of regenerable cells or protoplasts from the wild rocket plant or plant part of paragraph 4.

7. The tissue culture of paragraph 6, wherein said cells or protoplasts of the tissue culture are derived from a leaf, pollen, an embryo, a cotyledon, a hypocotyl, a meristematic cell, a root, a root tip, an anther, a flower, a seed or a stem.

8. A wild rocket plant regenerated from the tissue culture of paragraph 6 or 7, wherein the regenerated plant expresses all of the physiological and morphological characteristics of wild rocket variety 89-001 RZ a sample of seed of said variety having been deposited under NCIMB Accession No. 42516.

9. A method of vegetatively propagating a plant of wild rocket variety 89-001 RZ comprising (a) collecting tissue capable of being propagated from a plant of wild rocket 89-001 RZ, a sample of seed of said variety having been deposited under NCIMB Accession No. 42516, and (b) producing a rooted plant from said tissue.

10. A method of producing a wild rocket seed comprising crossing a male parent wild rocket plant with a wild rocket parent plant and harvesting the resultant wild rocket seed, wherein said male parent wild rocket plant and/or said female parent wild rocket plant is the wild rocket plant of paragraph 2.

11. A wild rocket seed produced by the method of paragraph 10.

12. A wild rocket plant produced by growing the seed of paragraph 11.

13. A method for producing a seed of a 89-001 RZ-derived wild rocket plant comprising (a) crossing a plant of wild rocket variety 89-001 RZ, representative seed of which having been deposited under NCIMB Accession No. 42516, with a second wild rocket plant, and (b) whereby seed of a 89-001 RZ-derived wild rocket plant forms.

14. The method of paragraph 13 further comprising (c) crossing a plant grown from 89-001 RZ-derived wild rocket seed with itself or with a second wild rocket plant to yield additional 89-001 RZ-derived wild rocket seed, (d) growing the additional 89-001 RZ-derived wild rocket seed of step (c) to yield additional 89-001 RZ-derived wild rocket plants, and (e) repeating the crossing and growing of steps (c) and (d) for an additional 3-10 generations to generate further 89-001 RZ-derived wild rocket plants, and (f) whereby seed of a 89-001 RZ-derived wild rocket plant forms.

15. A seed produced by the method of paragraphs 13 or 14.

16. A method of introducing at least one new trait into a plant of wild rocket variety 89-001 RZ comprising: (a) crossing a plant of wild rocket variety 89-001 RZ, representative seed of which having been deposited under NCIMB Accession No. 42516, with a second wild rocket plant that comprises at least one new trait to produce progeny seed; (b) harvesting and planting the progeny seed to produce at least one progeny plant of a subsequent generation, wherein the progeny plant comprises the at least one new trait; (c) crossing the progeny plant with a plant of wild rocket variety 89-001 RZ to produce backcross progeny seed; (d) harvesting and planting the backcross progeny seed to produce a backcross progeny plant; and (e) repeating steps (c) and (d) for at least three additional generations to produce a wild rocket plant of variety 89-001 RZ comprising at least one new trait and all of the physiological and morphological characteristics of a plant of wild rocket variety 89-001 RZ, when grown in the same environmental conditions.

17. A method of producing a plant of wild rocket variety 89-001 RZ comprising at least one new trait, the method comprising introducing a mutation or transgene conferring the at least one new trait into a plant of wild rocket variety 89-001 RZ, wherein a sample of seed of said variety has been deposited under NCIMB Accession No. 42516.

18. The wild rocket plant produced by the method of paragraph 16 or 17.

19. A method for producing wild rocket leaves as food product comprising sowing the seed of a paragraph 1 and growing the seed into a harvestable wild rocket plant and harvesting the leaves of said plant.

20. A method for producing wild rocket leaves as a fresh vegetable comprising packaging leaves of a plant of paragraph 2.

21. A method for producing wild rocket leaves as a processed food comprising processing leaves of a plant of paragraph 2.

22. A container comprising one or more wild rocket plants of paragraph 2 for harvest of leaves.

23. A method of determining the genotype of a plant of wild rocket variety 89-001 RZ, representative seed of which has been deposited under NCIMB Accession No. 42516, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of wild rocket variety 89-001 RZ and/or give rise to the expression of any one or more, or all, of the morphological and physiological characteristics of wild rocket variety 89-001 RZ of paragraph 2.

Having thus described in detail preferred embodiments of the present invention, it is to be understood that the inven- tion is not to be limited to particular details set forth in the above description as many apparent variations thereof are possible without departing from the spirit or scope of the present invention.

What is claimed is:

1. A seed of wild rocket variety 89-001 RZ, a sample of seed of said variety having been deposited under NCIMB Accession No. 42516.

2. A plant grown from the seed of claim 1.

3. The wild rocket plant of claim 2, which is a plant grown from seed having been deposited under NCIMB Accession No. 42516.

4. A wild rocket plant, or a part thereof, having all the physiological and morphological characteristics of the wild rocket plant of claim 2.

5. A part of the plant of claim 4, wherein said part is a microspore, pollen, an ovary, an ovule, an embryo sac or an egg cell, a cutting, a root, a stem, a cell or a protoplast.

6. A tissue culture of regenerable cells or protoplasts from the wild rocket plant or plant part of claim 4.

7. The tissue culture as claimed in claim 6, wherein said cells or protoplasts of the tissue culture are derived from a leaf, pollen, an embryo, a cotyledon, a hypocotyl, a meristematic cell, a root, a root tip, an anther, a flower, a seed or a stem.

8. A wild rocket plant regenerated from the tissue culture of claim 6 or 7, wherein the regenerated plant expresses all of the physiological and morphological characteristics of wild rocket variety 89-001 RZ a sample of seed of said variety having been deposited under NCIMB Accession No. 42516.

9. A method of vegetatively propagating a plant of wild rocket variety 89-001 RZ comprising (a) collecting tissue capable of being propagated from a plant of wild rocket 89-001 RZ, a sample of seed of said variety having been deposited under NCIMB Accession No. 42516, and (b) producing a rooted plant from said tissue.

10. A method of producing a wild rocket seed comprising crossing a male parent wild rocket plant with a wild rocket parent plant and harvesting the resultant wild rocket seed, wherein said male parent wild rocket plant and/or said female parent wild rocket plant is the wild rocket plant of claim 2.

11. A wild rocket seed produced by the method of claim 10.

12. A wild rocket plant produced by growing the seed of claim 11.

13. A method for producing a seed of a 89-001 RZ-derived wild rocket plant comprising (a) crossing a plant of wild rocket variety 89-001 RZ, representative seed of which having been deposited under NCIMB Accession No. 42516, with a second wild rocket plant, and (b) whereby seed of a 89-001 RZ-derived wild rocket plant forms.

14. The method of claim 13 further comprising (c) crossing a plant grown from 89-001 RZ-derived wild rocket seed with itself or with a second wild rocket plant to yield additional 89-001 RZ-derived wild rocket seed, (d) growing the additional 89-001 RZ-derived wild rocket seed of step (c) to yield additional 89-001 RZ-derived wild rocket plants, and (e) repeating the crossing and growing of steps (c) and (d) for an additional 3-10 generations to generate further 89-001 RZ-derived wild rocket plants, and (f) whereby seed of a 89-001 RZ-derived wild rocket plant forms.

15. A method of introducing at least one new trait into a plant of wild rocket variety 89-001 RZ comprising: (a) crossing a plant of wild rocket variety 89-001 RZ, representative seed of which having been deposited under NCIMB Accession No. 42516, with a second wild rocket plant that comprises at least one new trait to produce progeny seed; (b) harvesting and planting the progeny seed to produce at least one progeny plant of a subsequent generation, wherein the progeny plant comprises the at least one new trait; (c) crossing the progeny plant with a plant of wild rocket variety 89-001 RZ to produce backcross progeny seed; (d) harvesting and planting the backcross progeny seed to produce a backcross progeny plant; and (e) repeating steps (c) and (d) for at least three additional generations to produce a wild rocket plant of variety 89-001 RZ comprising at least one new trait and all of the physiological and morphological characteristics of a plant of wild rocket variety 89-001 RZ, when grown in the same environmental conditions.

16. A method of producing a plant of wild rocket variety 89-001 RZ comprising at least one new trait, the method comprising introducing a mutation or transgene conferring the at least one new trait into a plant of wild rocket variety 89-001 RZ, wherein a sample of seed of said variety has been deposited under NCIMB Accession No. 42516.

17. The wild rocket plant produced by the method of claim 15 or 16.

18. A method for producing wild rocket leaves as food product comprising sowing the seed of claim 1 and growing the seed into a harvestable wild rocket plant and harvesting the leaves of said plant.

19. A method for producing wild rocket leaves as a fresh vegetable comprising packaging leaves of the plant of claim 2.

20. A method for producing wild rocket leaves as a processed food comprising processing leaves of the plant of claim 2.

21. A container comprising at least one wild rocket plant of claim 2 for harvest of leaves.

22. A method of determining the genotype of a plant of wild rocket variety 89-001 RZ, representative seed of which has been deposited under NCIMB Accession No. 42516, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of wild rocket variety 89-001 RZ and/or give rise to the expression of any one or more, or all, of the morphological and physiological characteristics of wild rocket variety 89-001 RZ as claimed in claim 2.

* * * * *